US011133090B2

(12) United States Patent
McCallie, Jr. et al.

(10) Patent No.: US 11,133,090 B2
(45) Date of Patent: Sep. 28, 2021

(54) SEMANTIC SEARCH FOR A HEALTH INFORMATION EXCHANGE

(71) Applicant: CERNER INNOVATION, INC., Kansas City, KS (US)

(72) Inventors: David P. McCallie, Jr., Stilwell, KS (US); Christopher S. Finn, Liberty, MO (US); Margaret Cushing Kolm, Kansas City, MO (US)

(73) Assignee: CERNER INNOVATION, INC., Kansas City, KS (US)

( * ) Notice: Subject to any disclaimer, the term of this patent is extended or adjusted under 35 U.S.C. 154(b) by 735 days.

(21) Appl. No.: 15/713,262

(22) Filed: Sep. 22, 2017

(65) Prior Publication Data
US 2019/0095581 A1  Mar. 28, 2019

(51) Int. Cl.
*G16H 10/60* (2018.01)
*G06F 16/22* (2019.01)
*G06F 16/31* (2019.01)

(52) U.S. Cl.
CPC ......... *G16H 10/60* (2018.01); *G06F 16/2228* (2019.01); *G06F 16/313* (2019.01)

(58) Field of Classification Search
CPC .... G16H 10/60; G06F 16/313; G06F 16/2228
USPC ....................................................... 705/2–3
See application file for complete search history.

(56) References Cited

U.S. PATENT DOCUMENTS

| | | | |
|---|---|---|---|
| 7,742,933 B1* | 6/2010 | Royds | G16H 10/20 705/3 |
| 2008/0183495 A1* | 7/2008 | Butterfield | G16H 40/20 705/2 |
| 2009/0164474 A1* | 6/2009 | Noumeir | G16H 30/20 |
| 2011/0119088 A1* | 5/2011 | Gunn | G16H 10/60 705/3 |
| 2011/0196704 A1* | 8/2011 | Mansour | G06F 16/24564 705/3 |
| 2013/0124523 A1* | 5/2013 | Rogers | G16H 10/60 707/737 |
| 2015/0379210 A1* | 12/2015 | Serlie | G06F 19/00 705/3 |
| 2016/0042146 A1* | 2/2016 | Douglass | G06Q 30/0631 705/3 |
| 2017/0103163 A1* | 4/2017 | Emanuel | G16H 10/60 |
| 2018/0121843 A1* | 5/2018 | Connely, IV | G16B 20/10 |

* cited by examiner

*Primary Examiner* — Michael Tomaszewski
(74) *Attorney, Agent, or Firm* — Shook, Hardy & Bacon, L.L.P.

(57) ABSTRACT

A stateless, on-demand semantic indexing and search service for a health information exchange is provided that anticipatorily fetches data from one or more external sources, extracts semantic concepts from textual documents, and serves an in-memory semantic search index to users to ease finding of relevant patient data across a set of distributed health record data sources. Clinicians may search for not only text, but for semantic concepts, and the search index is able to return relevant results regardless of whether the source information is located inside or outside the local electronic health record. Predictive algorithms may be incorporated to pre-fetch, semantically process and index data for patients likely to be searched in an upcoming time window. Activity indicators for clinicians and patients may be utilized to pre-fetch, semantically process, and index data.

20 Claims, 6 Drawing Sheets

SEMANTIC SEARCH FOR A HEALTH INFORMATION EXCHANGE

BACKGROUND

Traditionally, a wealth of healthcare data exists with respect to a particular patient. However, the data is often dispersed throughout multiple sources and it is difficult to assimilate information from these multiple sources that is relevant to a particular clinician. Because of privacy and security concerns, there is often resistance to centralizing the data in one place on a permanent basis.

Although record viewing software is able to display and reconcile data from multiple sources, the ability to search for specific data elements by word, phrase, or semantic concept is not generally available due to reasons of privacy, confidentiality, security risk, cost, and lack of desirability around crawling, or extracting, data from a massive number of external data sources. In systems that support retrieval of data from many external systems, these factors result in design of systems in which data is not retrieved for a particular patient until a clinician requests, or is expected to request, data for that patient from sources external to the local health record. Even when that data is retrieved, its volume, and subsequent complications involved in data reconciliation, can overwhelm the clinician to the point that information relevant to the clinician cannot be easily found.

BRIEF SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present disclosure relate to systems, methods, and user interfaces providing a stateless, on-demand semantic indexing and search system (subsequently referred to as an "on-the-fly semantic search," where "on-the-fly" embodies the stateless and upon-demand aspects of the system) for a health information exchange. More particularly, embodiments of the present disclosure anticipatorily fetch data, extract semantic concepts from the data, index text and concepts into an inverted index, and provide a search capability permitting clinicians to search by words, and/or concepts and examine results in a viewer so that relevant data originating from external sources can easily be identified. Clinicians may search across local and internal data sources not only for text, but for semantic concepts, and the search index is able to return relevant results regardless of whether the source information is located inside or outside the local electronic health record. In other words, relevant data from outside the local record for the patient is provided to the clinician that may inform, supplement, or alert the clinician to information that is relevant to that clinician for that particular patient. In some embodiments, predictive algorithms may be incorporated to pre-fetch, semantically process and index data for patients likely to be searched in an upcoming time window. In some embodiments, contextual information and activity indicators for clinicians and patients may be utilized to pre-fetch, semantically process and index data.

BRIEF DESCRIPTION OF THE SEVERAL VIEWS OF THE DRAWINGS

The patent or application file contains at least one drawing executed in color. The present invention is described in detail below with reference to the attached drawing figures, wherein.

DETAILED DESCRIPTION

Figure 1:
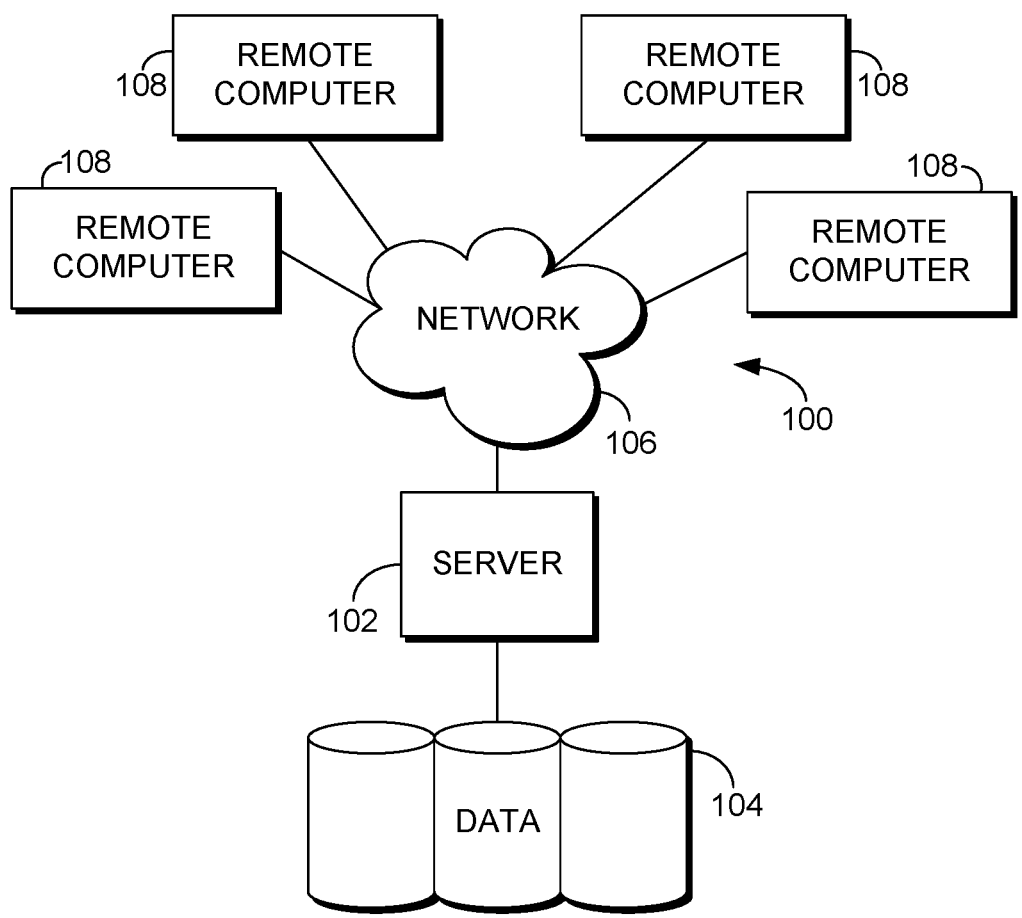
FIG. 1 is a block diagram of an exemplary operating environment suitable to implement embodiments of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" might be used herein to connote different elements of methods employed, the terms should not be interpreted as implying any particular order among or between various steps herein disclosed unless and except when the order of individual steps is explicitly stated.

As noted in the background, a wealth of healthcare data exists with respect to a particular patient. However, the data is often dispersed throughout multiple sources and it is difficult to assimilate information from these multiple sources that is relevant to a particular clinician. Because of privacy and security concerns, there is resistance to centralizing the data in one place.

Although some systems keep track of where data is maintained, neither a complete copy nor derived search index of that data spanning local and external sources is retained centrally due to the same privacy and security concerns. As a result, the complete and up-to-date data for a particular patient is not retrieved until a clinician requests data for that patient. Even when the data is retrieved, its volume, and subsequent complexity involved in data reconciliation, can overwhelm the clinician to the point the clinician cannot be easily found.

Embodiments of the present disclosure relate to systems, methods, and user interfaces providing a stateless, on-demand indexing and search system (referred to as "on-the-fly semantic search") for a health information exchange. More particularly, embodiments of the present disclosure anticipatorily fetch data from one of more external sources, extract semantic concepts from textual documents, and serves an in-memory semantic search index to users to ease finding of relevant patient data across a set of distributed health record data sources. By dynamically initiating the fetch, concept extraction, and serving of search index in a stateless fashion and upon demand, a number of benefits are realized, including vastly reduced infrastructure and processing costs, and improved performance. Clinicians may search for not only text, but for semantic concepts, and the search index is able to return relevant results regardless of whether the source information is located inside or outside the local electronic health record. In some embodiments, predictive algorithms may be incorporated to pre-fetch, semantically process, and index data for patients likely to be searched in an upcoming time window (e.g., based on census or admission information, etc.). In some embodiments, activity indicators for clinicians (e.g., opening a chart, clicking in a search window, etc.) that indicate that a search may happen may be utilized to pre-fetch, semantically process and index data.

Accordingly, one embodiment of the present disclosure is directed to a system for creating an on-the-fly index. The system includes an index engine that maintains an index for a subset of one or more patients and satisfies queries or indexing requests for the subset of one or more patients. The system also includes an in-memory document cache that, in memory using a stateless infrastructure and in response to the queries or indexing requests, stores patient-specific document sets, allows retrieval of individual documents or patient-specific document sets for a desired patient, or retains documents.

In another embodiment, the present disclosure directed to a computerized method for creating an on-the-fly index. The method comprises maintaining an index for a subset of one or more patients. The method also comprises, in response to receiving a query or an indexing request at the index, storing patient-specific document sets, allowing retrieval of individual documents or patient-specific document sets for a desired patient, or retaining documents in memory using a stateless infrastructure. The queries or indexing requests may be triggered by one of: a health information exchange (HIE) viewer process requesting clinical data from an interoperability network of electronic health records (EHRs), an HIE scheduler pre-fetching clinical data from an interoperability network of EHRs, or a user opening a chart for a new patient.

In yet another embodiment, the present disclosure is directed to one or more computer storage media having computer-executable instructions embodied thereon that, when executed by a computer, causes the computer to perform operations to facilitate creating an on-the-fly index. The operations include maintaining an index for a subset of one or more patients. The operations also include, in response to receiving a query or an indexing request at the index, storing patient-specific document sets, allowing retrieval of individual documents or patient-specific document sets for a desired patient, or retaining documents in memory using a stateless infrastructure.

Having briefly described embodiments of the present invention, an exemplary operating environment suitable for use in implementing embodiments of the present invention is described below. FIG. 1 provides an aspect of an example operating environment with which embodiments of the present invention may be implemented. The aspect of an operating environment is illustrated and designated generally as reference numeral 100.

Example operating environment 100 comprises a general purpose computing device in the form of a control server 102. Exemplary components of the control server 102 comprise a processing unit, internal system memory, and a suitable system bus for coupling various system components, including database cluster 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

Control server 102 typically includes therein, or has access to, a variety of computer-readable media, for instance, database cluster 104. Computer-readable media can be any available media that might be accessed by control server 102, and includes volatile and nonvolatile media, as well as, removable and nonremovable media. Computer-readable media might include computer storage media. Computer storage media includes volatile and nonvolatile media, as well as removable and nonremovable media implemented in any method or technology for storage of information, such as computer-readable instructions, data structures, program modules, or other data. In this regard, computer storage media might comprise RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the control server 102. Computer storage media does not comprise signals per se. Combinations of any of the above also may be included within the scope of computer-readable media.

The computer storage media discussed above and illustrated in FIG. 1, including database cluster 104, provide storage of computer-readable instructions, data structures, program modules, and other data for the control server 102. In some embodiments, data cluster 104 takes the form of a cloud-based data store, and in some embodiments is accessible by a cloud-based computing platform.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and providers' offices. Providers may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like.

The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

In some embodiments, remote computers 108 comprise computing-devices that are part of a cloud-computing platform. In some embodiments, a remote computer 108 is associated with a health records, data source such as an electronic health record (EHR) system of a hospital or medical organization, a health information exchange EHR, insurance provider EHR, ambulatory clinic EHR, or patient-sensor, or other data source, and facilitates accessing data of the source and communicating the data to control server 102 and/or other computing devices on a cloud computing platform, including other remote computers 108.

Exemplary computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networked environment, program modules or portions thereof might be stored in association with the control server 102, the database cluster 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a pointing device (commonly referred to as a mouse), a trackball, or a touch pad. Other input devices comprise microphones, satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

In some embodiments, control server 102 is a computing system or platform made up of one or more computing devices. Embodiments of control server 102 may be a distributed computing system, a centralized computing system, a single computer such as a desktop or laptop computer or a networked computing system. Thus, in some embodiments, control server 102 comprises a multi-agent computer system with software agents.

Figure 2:
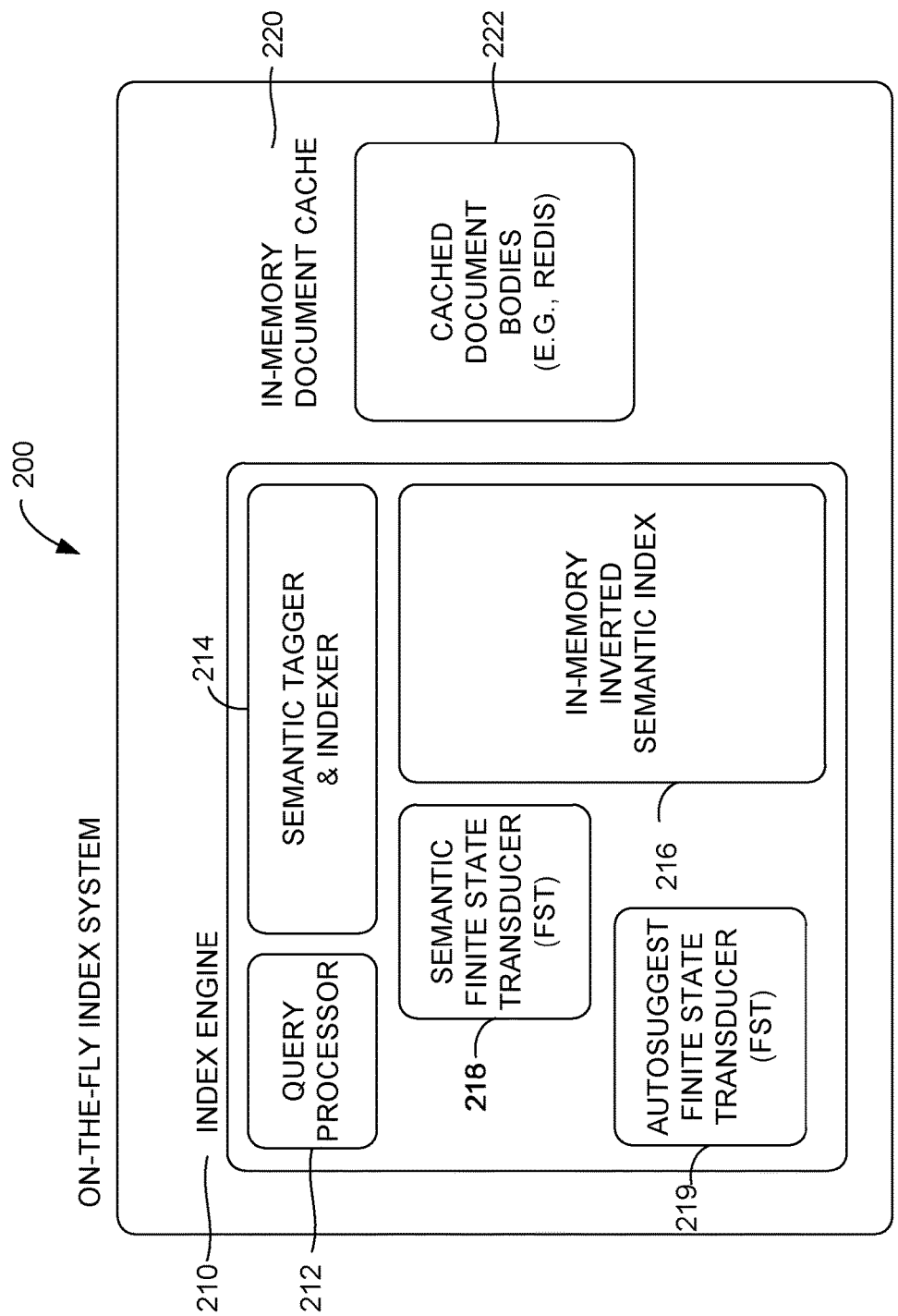
FIG. 2 depicts an exemplary framework of an on-the-fly index system suitable to implement embodiments of the present invention.

Turning now to FIG. 2, an exemplary framework of an on-the-fly index system 200 is shown, in accordance with an aspect of the present invention. It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by one or more entities may be carried out by hardware, firmware, and/or software. For instance, various functions may be carried out by a processor executing instructions stored in memory. The on-the-fly index system 200 may be implemented via any type of computing device, such as computing device 100 described above with reference to FIG. 1, for example.

The on-the-fly index system 200 generally operates to provide an on-the-fly semantic search for a health information exchange. In this way, the on-the-fly index system 200 anticipatorily fetches data, indexes it on-the-fly, and provides it in a viewer so relevant data originating from external sources can easily be identified. From a user perspective, it appears as though the user is able to select relevant data from a central index.

As shown in FIG. 2, the on-the-fly index system 200 includes, among other components not shown, an index engine 210 and an in-memory document cache 220. It should be understood that the on-the-fly index system 200 shown in FIG. 2 is an example of one suitable computing system architecture. Each of the components shown in FIG. 2 may be implemented via any type of computing device, such as computing device 100 described with reference to FIG. 1, for example.

The components may communicate with each other via a network, which may include, without limitation, one or more local area networks (LANs) and/or wide area networks (WANs). Such networking environments are commonplace in offices, enterprise-wide computer networks, intranets, and the Internet. It should be understood that any number of index engines and in-memory document caches may be employed within the on-the-fly index system 200 within the scope of the present disclosure. Each may comprise a single device or multiple devices cooperating in a distributed environment. For instance, the index engine 210 (or any of its components: query processor 212, semantic tagger and indexer 214, semantic finite state transducer (FST) 216, and in-memory inverted semantic index 218) and/or the in-memory document cache may be provided via multiple devices arranged in a distributed environment that collectively provide the functionality described herein. In other embodiments, a single device may provide the functionality of multiple components of the on-the-fly index system 200. For example, a single device may provide the index engine 210 and the in-memory document cache 220. In some embodiments, some or all functionality provided by the index engine 210 (or any of its components) and/or the in-memory document cache 220 may be provided by a user device. Additionally, other components not shown may also be included within the network environment.

Generally, the index engine 210 is a single, multi-threaded process responsible for maintaining the index for one or more patients, satisfying various queries, and indexing requests for the one or more patients, all in a stateless fashion. By being memory efficient and very fast, the need for disk access is obviated, since the semantic index can be constructed for arbitrary patients in sub-second time.

As described above, the index engine 210 includes several components including a query processor 212, a semantic tagger and indexer 214, a semantic FST 216, and an in-memory inverted semantic index. The query processor 212 initially provides two representational state transfer (RESTful) endpoints. The RESTful endpoints enable queries to be submitted against the index and partially typed (i.e., autosuggest) queries to be submitted against a patient-specific autosuggest FST 219 containing indexed terms and concepts that occur only in that patient's data.

The submitted queries are tokenized against the semantic FST in the same fashion described below with respect to the semantic tagger and indexer 214. This list of tokens can be utilized to retrieve sets of document lists from the in-memory inverted semantic index 218 along with associated term frequency-index document frequency (TF-IDF) scores. The retrieved documents can be scored and weighted by prominence and frequency of tokens in the query string to achieve a ranked list of query results. The ranked list of query results may include document ID, ranking score, a list of positional information (character ranges) by token for each query token's intersection with a document, and the most relevant "snippet" (contextual summary of the token in text as referenced against the in-memory document cache 220) for each query token.

Partially-typed data POSTed to the query processor 212 is submitted to the autosuggest FST 219 for the patient. In response, lists of terms or concepts present in the patient's index that either match the substring, start with the substring, or are lexically close in proximity to the substring are returned. Additionally, a count of documents in the index associated with each returned term or concept is returned.

The semantic tagger and indexer 214 initially provides a RESTful interface to accept POSTed clinical data. A raw copy of the POSTed clinical data is stored in the in-memory document cache 220 along with other cached document bodies 222. Each document is assigned a unique document identification (ID).

Indexable tokens are parsed from each of the submitted documents and are submitted to the semantic FST 218 to identify multi-token concepts to tag and include in the index. For each token (e.g., a word or a concept), the token tuple (token index entry, position range in document, document ID) is added to the appropriate patient's instance of an in-memory inverted semantic index 216. Before completing processing of the POST, the autosuggest FST 219 is updated to reflect tokens in the index for the patient.

The in-memory inverted semantic index 216 stores all indexed tokens with POST lists (i.e., document IDs, result IDs) along with position offset lists of where those tokens are located in respective documents. All items are stored in-memory in a compressed and memory-optimized format.

The index entry (or token) list is retrievable for construction of the per-patient autosuggest FST 219. Methods for retrieving lists of documents corresponding to sets of requested index tokens are also provided. For each index entry, a running TF-IDF score specific to the patient the index represents is maintained.

The semantic FST 218 initially, at system initialization, at system initialization, loads a nomenclature of concept codes and associated strings and string variations into a FST map memory structure. Features of this structure include optimal memory efficiency, ability to perform Levenshtein and fuzzy searches for map keys, sub-linear memory growth for map entries (relative to string size), support for misspelling and character transposition, and the ability to distinguish between partial and full map key matches. For example, searching for "heart" can determine if "heart" is the only term present, or whether longer terms starting with "heart", such as "heart attack", are available as keys.

The semantic tagger and indexer 214 probes the FST map for token matches. The probing progresses until terminal searches are encountered (e.g., responses from the semantic FST 218 that matches no longer exist). For each match identified, the code associated with the matched concept is returned.

The autosuggest FST 219 is responsible for constructing an FST that maps terms and/or concepts in the patient's index to the counts of documents containing each term and/or concept. The autosuggest FST accomplishes this in a highly memory-efficient, compressed format. The autosuggest FST 219 also responds to requests for complete, partial, and lexically-similar terms and/or concepts in the FST, along with corresponding document counts.

The in-memory document cache 220 is a separate process that can be hosted on the same physical hardware as the index engine 210 for reduced latency, or can be hosted on separate hardware as the index engine 210 for scalability. The in-memory document cache 220 stores patient-specific document sets. Each document is an indexable entity, such as a clinical document, a clinical result, or metadata.

In embodiments, the in-memory document cache 220 allows retrieval of individual documents (as described above) or document sets for a desired patient. The documents can be retained in memory using a stateless infrastructure such as, for example, REDIS (an in-memory cache with optional persistence).

Figure 3:
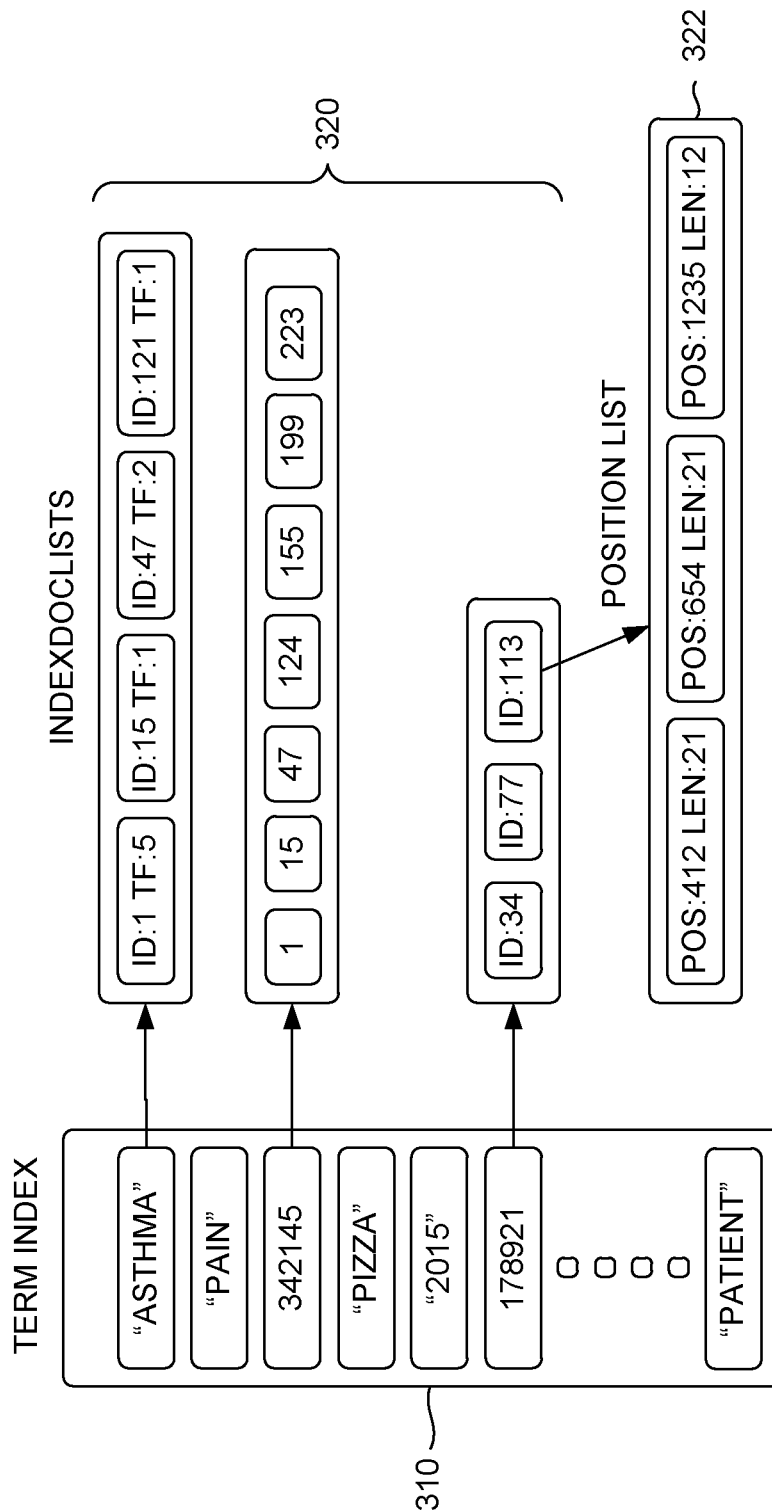
FIG. 3 depicts an exemplary index in accordance with an embodiment of the present invention.

Referring now to FIG. 3, an exemplary index illustrates how each unique term is identified in the index. A term index 310 includes a hash map with an entry for each unique term or concept code. The value for each item in the index is an index document list 320. The index document list 320 includes a list of document entries (identification of the document, term frequency, and a list of positions 322 a term or concept appears in the document).

Figure 4:
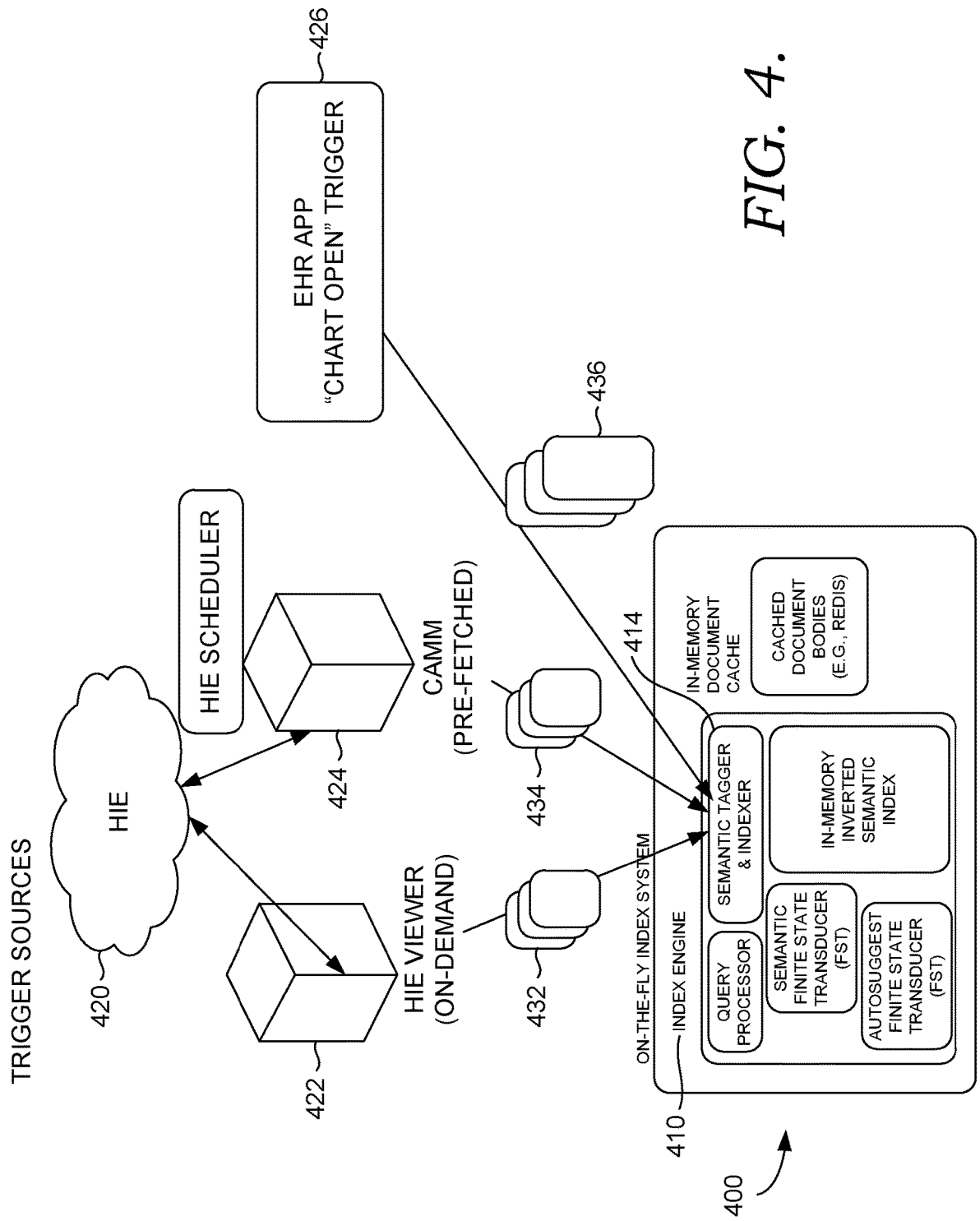
FIG. 4 depicts an exemplary framework of an on-the-fly index system and its triggers suitable to implement embodiments of the present invention.

In practice, and referring now to FIG. 4, upon the clinician searching for a particular keyword, the system retrieves data corresponding to the keyword, indexes it, and provides the index to the clinician for selection of relevant data. In other words, relevant data from outside the local record for the patient is provided to the clinician that may conflict, supplement, or alert the clinician to information that is relevant to that clinician for that particular patient. In some embodiments, predictive algorithms may be incorporated to pre-fetch and index data for patients likely to be searched in an upcoming time window. In some embodiments, contextual information may be utilized to pre-fetch and index data.

For example, indexing may be triggered in a variety of ways, resulting in clinical data 432, 434, 436 being posted to the RESTful interface of the semantic tagger and indexer 414. In one embodiment, a health information exchange (HIE) viewer 422 process requests clinical data 432 from an interoperability network of EHRs (i.e., the HIE 420) and POSTs the clinical data 432 to the index engine 410.

In another embodiment, a HIE scheduler 424 pre-fetches clinical data 434 from an interoperability network of EHRs (i.e., the HIE 420), caches for HIE purposes, and POSTs the clinical data 434 to the index engine 410.

In another embodiment, when a user opens a chart for a new patient (such as via an EHR application 426), a trigger POSTs the clinical data 436 to the index engine 410.

Figure 5:
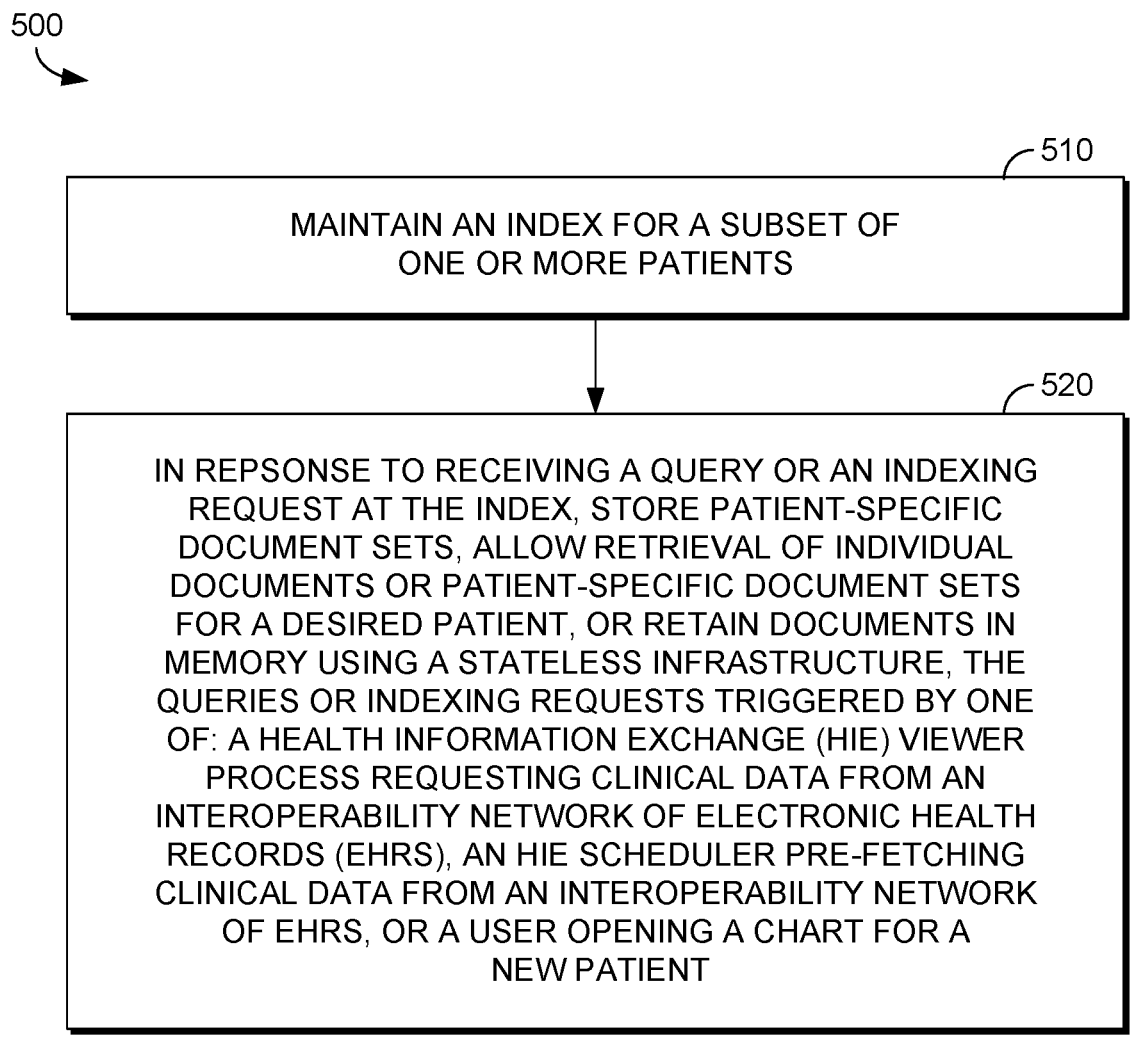
FIG. 5 depicts a flow diagram of a method for creating an on-the-fly index, in accordance with an embodiment of the present invention.

Turning now to FIG. 5, a flow diagram is provided illustrating a method 500 for creating an on-the-fly index instance, in accordance with embodiments of the present invention. Method 500 may be performed by any computing device (such as computing device described with respect to FIG. 1) with access to an on-the-fly index system (such as the one described with respect to FIGS. 2 and 4) or by one or more components of the on-the-fly index system.

Initially, at step 510, an index is maintained for a subset of one or more patients. In response to receiving a query or an indexing request at the index, storing patient-specific document sets, allowing retrieval of individual documents or patient-specific document sets for a desired patient, or retaining documents in memory using a stateless infrastructure, at step 520. The queries or indexing requests can be triggered by one of: a health information exchange (HIE) viewer process requesting clinical data from an interoperability network of electronic health records (EHRs), an HIE scheduler pre-fetching clinical data from an interoperability network of EHRs, or a user opening a chart for a new patient.

Figure 6:
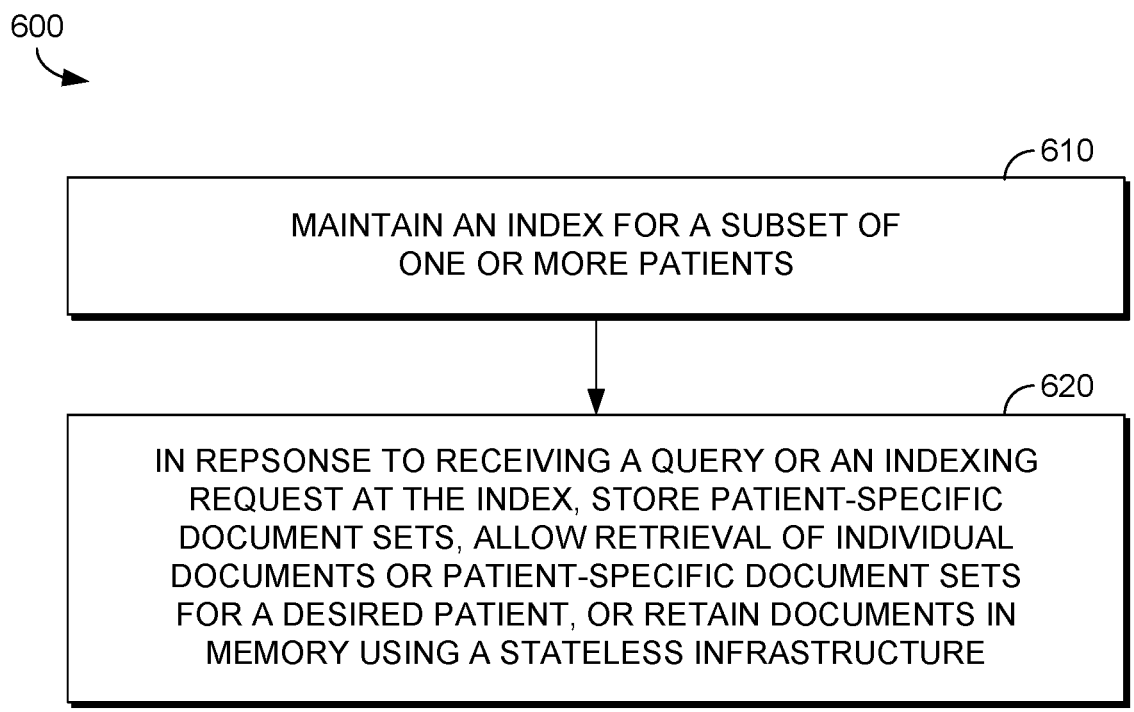
FIG. 6 is a flow diagram of a method for creating an on-the-fly index, in accordance with embodiments of the invention.

Turning now to FIG. 6, a flow diagram is provided illustrating a method 600 for creating an on-the-fly index instance, in accordance with embodiments of the present invention. Method 600 may be performed by any computing device (such as computing device described with respect to FIG. 1) with access to an on-the-fly index system (such as the one described with respect to FIGS. 2 and 4) or by one or more components of the on-the-fly index system.

Initially, at step 610, an index is maintained for a subset of one or more patients. In response to receiving a query or an indexing request at the index, storing patient-specific document sets, allowing retrieval of individual documents or patient-specific document sets for a desired patient, or retaining documents in memory using a stateless infrastructure, at step 620.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. A system for creating an on-the-fly index, the system comprising:
   a health information exchange (HIE) scheduler that prefetches, utilizing contextual information and activity indicators for clinicians and patients, clinical data from an interoperability network of EHRs, wherein prefetching triggers indexing requests at an index engine;
   the index engine that maintains an index for a subset of one or more patients and satisfies the indexing requests for the subset of one or more patients; and
   an in-memory document cache that, in memory using a stateless infrastructure and in response to the indexing requests, stores patient-specific document sets, allows retrieval of individual documents or patient-specific document sets for a desired patient, or retains documents.

2. The system of claim 1, wherein the indexing requests are triggered by a user opening a chart for a new patient.

3. The system of claim 1, wherein the index engine includes a semantic tagger and indexer.

4. The system of claim 3, wherein the semantic tagger and indexer provides an interface to accept clinical data provided at the on-the-fly index.

5. The system of claim 4, wherein the semantic tagger and indexer provides documents to be stored at the in-memory document cache, the document being a copy of the accepted clinical data.

6. The system of claim 5, wherein the semantic tagger and indexer assigns a document identification (ID) that is unique for each document.

7. The system of claim 6, wherein the semantic tagger and indexer parses indexable tokens for each document.

8. The system of claim 7, wherein the semantic tagger and indexer submits groups of tokens to a semantic finite state transducer to identify multi-token concepts to tag and include in the on-the-fly index.

9. The system of claim 8, wherein the semantic tagger and indexer adds a token tuple for each token to a patient instance of an inverted semantic index.

10. The system of claim 9, wherein the semantic tagger and indexer updates an autosuggest finite state transducer to reflect tokens in the index before the on-the-fly index is created for the patient.

11. The system of claim 1, wherein the index engine includes an in-memory inverted semantic index.

12. The system of claim 11, wherein the in-memory inverted semantic index stores indexed tokens with post lists and position offset lists to identify where the indexed tokens are located in respective documents.

13. The system of claim 12, wherein an index entry or token list is retrievable for construction of a patient-specific autosuggest finite state transducer.

14. The system of claim 1, wherein the index engine includes a semantic finite state transducer that, at system initialization, loads a nomenclature of concept codes and associated strings and string variations into a finite state transducer (FST) memory structure.

15. The system of claim 14, wherein a semantic tagger and indexer probes the FST memory structure for token matches.

16. The system of claim 1, wherein the index engine includes a query processor that utilizes a list of tokens to retrieve sets of documents lists from an inverted index.

17. The system of claim 1, wherein the index engine includes a query processor that receives partially-typed query and submits it to an autosuggest finite state transducer (FST), the autosuggest FST returning lists of terms or concepts present in a patient index that match a partially-typed query, start with the partially-typed query, or are lexically close in proximity to the partially-typed query, along with a count of documents in the on-the-fly index associated with each returned term or concept.

18. The system of claim 1, wherein the index engine includes an autosuggest finite state transducer (FST) that constructs a FST that maps terms and concepts in a patient index to counts of documents containing each term or concept and responds to requests for complete, partial, and lexically-similar terms or concepts in the FST, along with a count of documents in the on-the-fly index associated with each returned term or concept.

19. A computerized method for creating an on-the-fly index, the method comprising:
   maintaining an index for a subset of one or more patients;
   in response to receiving an indexing request at the index, storing patient-specific document sets, allowing retrieval of individual documents or patient-specific document sets for a desired patient, or retaining documents in memory using a stateless infrastructure, the indexing requests triggered by contextual information and activity indicators for clinicians and patients.

20. One or more computer storage media having computer-executable instructions embodied thereon that, when executed by a computer, causes the computer to perform operations to facilitate creating an on-the-fly index, the operations comprising:
   maintaining an index for a subset of one or more patients;
   pre-fetching, utilizing contextual information and activity indicators for clinicians and patients at a health information exchange (HIE) scheduler, clinical data from an interoperability network of EHRs, the pre-fetching triggering an indexing request;
   in response to the indexing request being triggered at the index, storing patient-specific document sets, allowing retrieval of individual documents or patient-specific document sets for a desired patient, or retaining documents in memory using a stateless infrastructure.

\* \* \* \* \*